US006433166B2

(12) United States Patent
Shimazu et al.

(10) Patent No.: US 6,433,166 B2
(45) Date of Patent: Aug. 13, 2002

(54) PROCESS FOR PRODUCING ε-CAPROLACTAM

(75) Inventors: Yasumoto Shimazu; Hiroyuki Umida, both of Niihama; Masami Fukao, Shiga, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/887,360

(22) Filed: Jun. 25, 2001

(30) Foreign Application Priority Data

Jun. 27, 2000 (JP) ........................................ 2000-192350

(51) Int. Cl.[7] ........................................... C07D 201/16
(52) U.S. Cl. ...................................................... 540/540
(58) Field of Search ........................................ 540/540

(56) References Cited

U.S. PATENT DOCUMENTS

| | | | | |
|---|---|---|---|---|
| 3,792,045 A | * | 2/1974 | Henn et al. ........... | 260/239.3 A |
| 3,794,647 A | * | 2/1974 | Henn et al. ........... | 260/239.3 A |
| 3,839,324 A | * | 10/1974 | Schnultze et al. .... | 260/239.3 A |
| 4,709,024 A | | 11/1987 | Sato et al. ............ | 540/536 |
| 4,717,769 A | | 1/1988 | Sato et al. ............ | 540/536 |
| 4,963,673 A | | 10/1990 | Merger et al. ........ | 540/538 |
| 5,495,016 A | | 2/1996 | Achhammer et al. ....... | 540/539 |
| 6,252,068 B1 | * | 6/2001 | Fukao et al. ................ | 540/540 |

FOREIGN PATENT DOCUMENTS

| | | |
|---|---|---|
| DE | 2203945 A | 8/1973 |
| DE | 2163259 B | 2/1976 |
| EP | 0 311 960 A2 | 4/1989 |
| EP | 0337323 A2 | 10/1989 |
| EP | 0 570 110 A1 | 4/1993 |
| EP | 0 635 487 A1 | 1/1995 |
| EP | 0 943 608 A1 | 1/1995 |
| EP | 0 641 778 A1 | 3/1995 |
| EP | 1 016 658 A2 | 7/2000 |
| JP | 9003041 | 1/1997 |

* cited by examiner

*Primary Examiner*—Bruck Kifle
(74) *Attorney, Agent, or Firm*—Birch, Stewart, Kolasch & Birch, LLP

(57) ABSTRACT

A high purity ε-caprolactam is prepared by pouring a molten crude ε-caprolactam and a solvent comprising an aliphatic hydrocarbon and having a lower temperature than that of the crude ε-caprolactam, into a vessel and mixing them to obtain a first slurry containing a crystallized ε-caprolactam. The slurry is then subjected to a solid-liquid separation to obtain ε-caprolactam and a first liquid phase. This process can effectively remove impurities from a crude ε-caprolactam, which is obtained by for example, subjecting cyclohexanone oxime to the Beckmann rearrangement.

32 Claims, 1 Drawing Sheet

PROCESS FOR PRODUCING ε-CAPROLACTAM

FIELD OF THE INVENTION

The present invention relates to a process for producing ε-caprolactam and, in particular, a process for producing a high-purity ε-caprolactam by crystallizing ε-caprolactam from crude ε-caprolactam which contains impurities.

BACKGROUND OF THE INVENTION

ε-Caprolactam is an important compound is which used as an intermediate for the preparation of polyamides such as Nylon-6, and many processes are known to produce ε-caprolactam. For example, ε-caprolactam has been produced by subjecting cyclohexanone oxime to Beckmann rearrangement in the presence of an acidic medium such as fuming sulfuric acid. This process has drawbacks including the production of a large amount of ammonium sulfate.

The above process is improved by gas phase Beckmann rearrangement using a solid catalyst. Solid catalysts used for the gas phase Beckmann rearrangement include boric acid catalysts, silica-alumina catalysts, solid phosphoric acid catalysts, complex metal oxide catalysts, zeolite catalysts, etc. Furthermore, JP-A-62-123167 (corresponding to U.S. Pat. No. 4,709,024) and JP-A-63-54358 (corresponding to U.S. Pat. No. 4,717,769) disclose the use of high silica metallosilicate catalysts for the production of ε-caprolactam.

Processes for producing ε-caprolactam, which are not based on the Beckmann rearrangement, are also known. For example, JP-A-2-215767 discloses a process comprising the step of cycling methyl6-aminocaproate to obtain ε-caprolactam, U.S. Pat. No. 5,495,016 discloses a process comprising the step of reacting 6-aminocapronitrile with water to obtain ε-caprolactam, and JP-A-9-3041 discloses a process comprising the step of reacting methyl 6-hydroxycaproate with ammonia in the presence of hydrogen and steam to obtain ε-caprolactam.

Also, crude ε-caprolactam is obtained in a process of depolymerizing, at a high temperature, oligomers and polymers containing Nylon-6 which are recovered in the production of Nylon-6.

However, ε-caprolactam obtained by the above-described processes contains various impurities. As is well known, ε-caprolactam is used as a raw material for the preparation of polyamide, and the ε-caprolactam utilized to prepare polyamide for producing synthetic fibers or films is required to have high purity. Thus, the ε-caprolactam prepared by the above processes, that is the crude ε-caprolactam containing impurities, is first purified by various purification methods such as crystallization, extraction, distillation and hydrogenation to obtain a high purity ε-caprolactam, which is then utilized.

Among the purification methods, crystallization is known to be a method in which quite a few kinds of impurities can be removed all at once. However, a generally known crystallization method such as a crystallization with cooling has problems. For example, when the crystallization with cooling is conducted continuously, effective removal of heat of the crystallization is needed. Therefore, the difference in temperature between an ε-caprolactam solution and a medium for cooling needs to be large such that a tank for crystallization and/or crystallizer needs to have a huge cooling surface area. In addition, since ε-caprolactam deposits (so-called scales) are easily produced at the cooling surface of the tank or the crystallizer, a specific tank or crystallizer is needed such as a crystallization vessel with a scraper (which is used for the removal of scales) or a multistage crystallizer in which the difference in temperature between an ε-caprolactam solution and a medium for cooling is small to reduce the scale generation on an inner wall of the crystallizer. Such specific tank and crystallizer are expensive and make a plant cost high.

JP-A-1-261,363 discloses another crystallization method of reducing the pressure in a tank in which the crystallization is conducted, to utilize latent heat of evaporation for removing the heat of crystallization therein. This method also needs specific equipment such as a vacuum pump and a vacuum crystallizer and, therefore, again makes plant cost high.

SUMMARY OF THE INVENTION

The present inventors have conducted extensive research with the object of providing a process for producing an ε-caprolactam having a high quality, the process industrially removing impurities continuously from crude ε-caprolactam in an efficient and economical way. As a result, it has been found that such a production process is provided by purifying crude ε-caprolactam in a crystallization method in which molten, crude ε-caprolactam and a cooled solvent are poured into a vessel. The present invention has been accomplished on the bases of the findings.

The present invention provides a process for producing ε-caprolactam, comprising the steps of:

(i) pouring molten, crude ε-caprolactam and a solvent into a vessel, the solvent comprising an aliphatic hydrocarbon and having a temperature lower than the temperature of the crude ε-caprolactam, and mixing the ε-caprolactam and solvent to obtain a first slurry containing crystallized ε-caprolactam, and (ii) subjecting the first slurry to a solid-liquid separation to obtain ε-caprolactam and a first liquid phase.

DETAILED DESCRIPTION OF THE INVENTION

Figure 1:
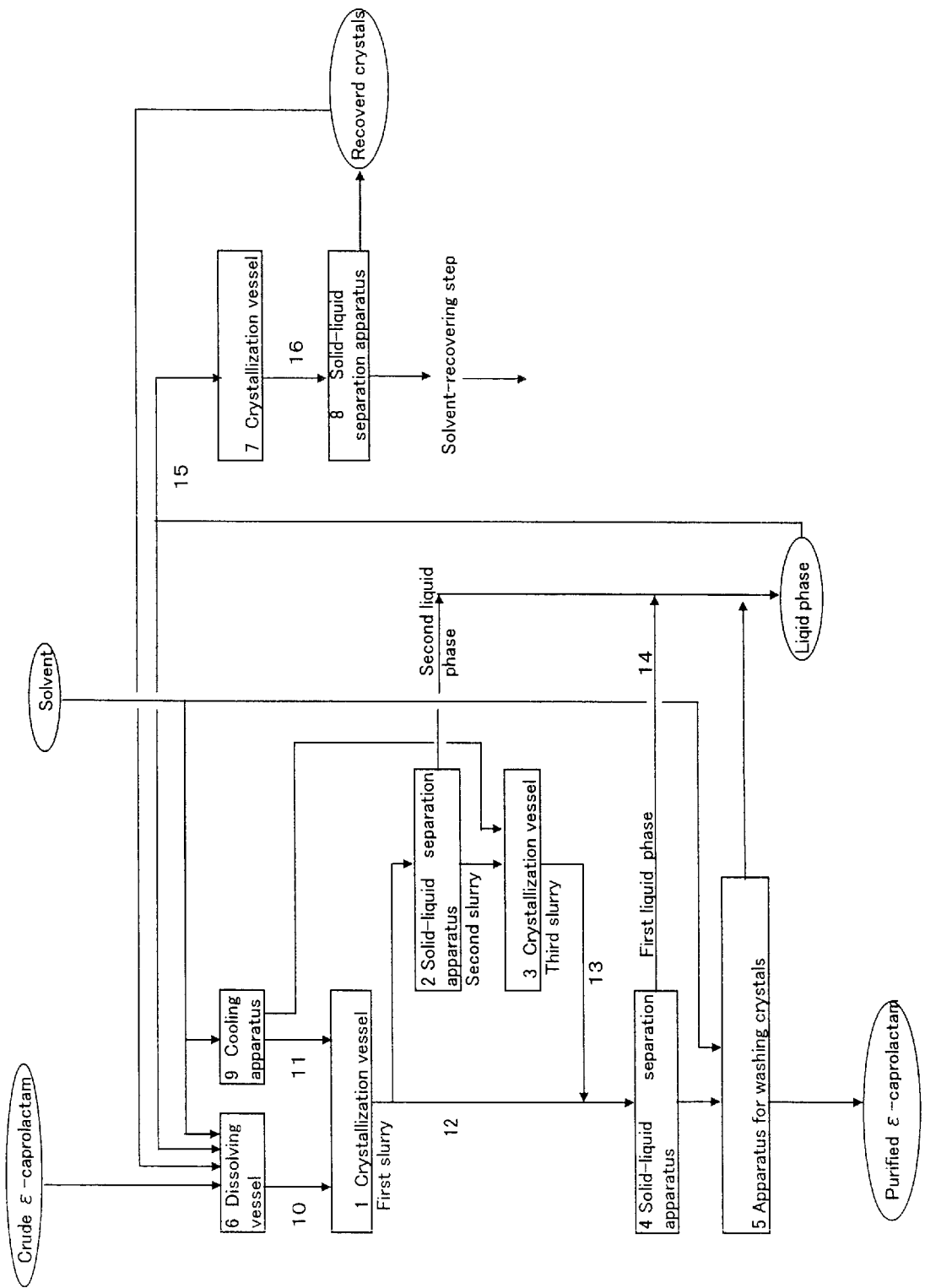
FIG. 1 is a flow chart illustrating an embodiment of the process of the present invention.

In the present invention, an ε-caprolactam containing impurities (that is a crude ε-caprolactam) is purified by crystallization to produce a high quality ε-caprolactam. The present invention may be applied for any crude ε-caprolactam such as the crude ε-caprolactam obtained by the above-described known processes.

Hereinafter, an embodiment of the present invention is described with reference to crude ε-caprolactam obtained by gas phase Beckmann rearrangement of cyclohexanone oxime in the presence of a zeolite-type catalyst such as a metallosilicate or a silicalite. Of course, as would be apparent to one skilled in the art, the present invention may be used to treat crude ε-caprolactam prepared by any suitable process.

In the present invention, molten, crude ε-caprolactam and a solvent comprising an aliphatic hydrocarbon and having a lower temperature than that of the crude ε-caprolactam, are preferably poured together into a vessel and are mixed with each other to obtain a slurry (which is a first slurry) containing a crystallized ε-caprolactam (step(i)), and then the obtained first slurry is subjected to a solid-liquid separation (step (ii)).

The solvent comprising an aliphatic hydrocarbon (utilized in step (i)) may further contain an organic solvent having a higher polarity than that of the aliphatic hydrocarbon.

The molten crude ε-caprolactam may itself contain a solvent comprising an aliphatic hydrocarbon which may be the same or different from the aliphatic hydrocarbon contained in the solvent added to the ε-caprolactam, or may contain a solvent comprising an aliphatic hydrocarbon which again may be the same or different from the aliphatic hydrocarbon contained in the solvent added to the ε-caprolactam, and an organic solvent having a higher polarity than that of the aliphatic hydrocarbons.

In the pouring of step (i), the solvent comprising an aliphatic hydrocarbon has a lower temperature than that of the molten crude ε-caprolactam. The temperature of the solvent and that of the molten crude ε-caprolactam are not limited as long as the former is lower than the latter. The temperature of the solvent may fall within the range of from about −30° C. to about 40° C., preferably within the range of from about −10° C. to about 30° C. The temperature of the molten crude ε-caprolactam may fall within the range of from about 40° C. to about 90° C., preferably within the range of from about 55° C. to about 80° C. When the molten crude ε-caprolactam does not contain a solvent comprising an aliphatic hydrocarbon or a solvent comprising an aliphatic hydrocarbon and an organic solvent having a higher polarity than that of the aliphatic hydrocarbon, then the temperature of the crude ε-caprolactam may fall within the range of from about 65° C. to about 90° C., preferably within the range of from about 70° C. to about 80° C. When the molten crude ε-caprolactam contains any of those solvents, then the temperature of the crude ε-caprolactam with the solvent may fall within the range of from about 40° C. to about 80° C., preferably within the range of from about 55° C. to about 75° C. Each pouring of the molten crude ε-caprolactam and the solvent comprising an aliphatic hydrocarbon is preferably carried out together into a vessel and may be conducted simultaneously and continuously. Alternatively, each pouring thereof may be conducted separately in turn as long as the advantages of the present invention are not deteriorated.

Once the molten crude ε-caprolactam and the lower-temperature solvent comprising an aliphatic hydrocarbon are poured into a vessel and are mixed with each other, ε-caprolactam is crystallized to obtain a first slurry containing the crystalline ε-caprolactam. In the crystallization, heat of crystallization therein and sensible heat of the solvent may compensate each other to maintain the temperature of the resulting slurry constant. The slurry may be subjected to aging if necessary to have the crystals therein become enlarged and be continuously sent into a solid-liquid separation step (ii) to separate and remove ε-caprolactam crystals and a liquid phase therefrom.

The crude ε-caprolactam contains impurities such as methanol (that is used as a solvent in a Beckmann rearrangement reaction) and cyclohexanone oxime (that is an unreacted raw material in the reaction) as well as many kinds of by-products including cyclohexanone, cyclohexenone, n-hexanitrile, 5-hexenitrile, metyllactam, caprenolactams such as 1,3,4,5-tetrahydroazepine-2-one, 1,5,6,7-tetrahydroazepine-2-one and structural isomers thereof, 1,2,3,4,6,7,8,9-octahydrophenazine (hereinafter, referred to as "OHP") and amines such as 3-N-methyl-4,5,6,7-tetrahydrobenzimidazole (hereinafter, referred to as "MTHI"). For example, the crude ε-caprolactam obtained by the gas phase Beckmann rearrangement of cyclohexanone oxime may contain 10 ppm or more of cyclohexanone oxime, 10 ppm or more of OHP, 25 ppm or more of MTHI and 25 ppm or more of caprenolactams, based on the ε-caprolactam. In the crystallization method of the present invention, these impurities and by-products (except for caprenolactams) may be separated from the crude product all at once.

The crude ε-caprolactam obtained by the gas phase Beckmann rearrangement of cyclohexanone oxime in the presence of a zeolite type catalyst may contain other kinds of by-products having a low boiling point or a high boiling point as well as a solvent such as methanol. In order to improve efficiency of purification in the present invention, it is preferred to carry out a preliminary purification such as distillation prior to the purification by crystallization in step (i) if desired, to remove all or a part of the solvent and the by-products from the ε-caprolactam.

In the present invention, a solvent having a low polarity (specifically, a solvent comprising an aliphatic hydrocarbon) is utilized in the purification by crystallization of ε-caprolactam in step (i). The conventional crystallization method of ε-caprolactam, in which ε-caprolactam is crystallized using water or an organic solvent having a high polarity, has many problems such that yield of ε-caprolactam tends to decrease since a large amount of ε-caprolactam dissolves in such a solvent or water, and the obtained ε-caprolactam tends to be contaminated by the impurities since the content of impurities contained in a liquid portion adherent to the t-caprolactam is high.

Examples of aliphatic hydrocarbon that may be utilized in the crystallization step (i) include linear aliphatic hydrocarbons having 6 to 12 carbon atoms, side-chain aliphatic hydrocarbons having 6 to 12 carbon atoms, alicyclic hydrocarbons having 6 to 12 carbon atoms, etc. Specific examples thereof include linear aliphatic hydrocarbons such as hexane, n-heptane, n-octane, n-nonane and n-decane; side-chain aliphatic hydrocarbons such as methylhexane, isooctane and neohexane; and alicyclic hydrocarbons such as methylcyclopentane, cyclohexane and methylcyclohexane. Among them, it is preferred to use an aliphatic hydrocarbon having a boiling point which is higher than a melting point of ε-caprolactam and lower than a boiling point of ε-caprolactam (especially that having a boiling point of about 150° C. or lower). Specific preferable examples include cyclohexane, n-heptane, isooctane and petroleum ether. These aliphatic hydrocarbons may be used singly or in admixture of two or more of them or together with an organic solvent having a higher polarity and being uniformly miscible with them. Together with the above aliphatic hydrocarbon, may be utilized a small amount of an organic solvent having a lower polarity and being usually immiscible with the aliphatic hydrocarbons, for example, an aromatic hydrocarbon such as benzene, toluene and xylene, an aliphatic hydrocarbon halide such as trichloroethylene, an ether such as propyl ether and isopropyl ether, an ester such as ethyl acetate, isopropyl acetate or an alcohol ethanol and iso-propanol, as long as the removal of the impurities is not interfered.

When an aliphatic hydrocarbon is utilized in admixture of two or more thereof or together with other solvents described above, it is preferred that both of those hydrocarbon/solvents have low polarities and boiling points which are close to one another. In such a preferable case, a large amount of those hydrocarbon/solvents can be utilized in the crystallization step (i) and provide less influence to the crystallization yield even when a composition ratio of the aliphatic hydrocarbon to those hydrocarbon/solvents in the mixture thereof varies, since solubility of ε-caprolactam in the mixture is low. In such a case, it is easy to control the composition ratio of the mixture. Such a case may be preferably provided by a combination of linear or chain aliphatic hydrocarbon with an alicyclic hydrocarbon, especially preferred is a combination of n-heptane with cyclohexane.

The amount of solvent comprising an aliphatic hydrocarbon utilized for crystallization is not limited and an optimum amount thereof varies depending on the conditions (such as a temperature) during crystallization. The amount may fall within the range of from about 0.5 part by weight to about 5 parts by weight, and preferably is within the range of from about one part by weight to about 4 parts by weight, based on one part by weight of ε-caprolactam to be crystallized. Although not outside the scope of the present invention, when the amount of solvent exceeds the above upper limit, the effects on the crystallization may not be improved in proportion to the increased amount of solvent, and costs to recover the solvent may increase. Also again while not outside the scope of the present invention, when the amount of solvent is too small, sufficiently purified crystals of ε-caprolactam may not be obtained.

The crystallization temperature of the process of the present invention may be from about 100° C. to less than the melting point of ε caprolactam, preferably from about 30° C. to about 60° C., more preferably from about 40° C. to about 60° C. A higher temperature is preferred as long as the temperature does not significantly influence yield of ε-caprolactam, since the amount of heat which should be removed during crystallization is small and impurities is easily separated.

An outer surface of the crystallization vessel may be covered with a heat insulating material. The temperature of an inner surface of the vessel may be kept at the same (or a little bit higher) temperature as (or than) the crystallization temperature so that crystals of ε-caprolactam are not deposited onto the surface of the vessel. Specifically, the temperature is preferably kept higher than the crystallization temperature by about 5° C. or lower, preferably by about 1° C. or lower, so that the scale generation can be suppressed.

The crystallization step (i) of the present invention may be conducted by a method whereby a crude ε-caprolactam in a molten state and a solvent comprising an aliphatic hydrocarbon are continuously poured at a constant rate into a vessel and are mixed with each other to crystallize ε-caprolactam, while the temperature in the vessel is kept at a prescribed temperature. Before being mixed with the solvent comprising the aliphatic hydrocarbon, the molten crude ε-caprolactam may previously contain the same kind of solvent. In this case, if such an ε-caprolactam containing solvent is cooled (prior to being poured to the vessel) to the temperature such that ε-caprolactam does not crystallize therein, the amount of specific impurities (such as cyclohexanone oxime) remaining in the crystallized ε-caprolactam can be reduced compared with the case in which an ε-caprolactam containing no solvent is utilized, even if the ratio of the total amount of solvent used in the crystallization step to the crude ε-caprolactam is the same in both cases.

When aging is conducted, then a solids content (i.e. slurry concentration) of the slurry containing the crystallized ε-caprolactam may be stabilized. The time for aging may fall within the range of from about 5 minutes to about 60 minutes, and preferably is within the range of from about 20 minutes to about 40 minutes. The time for aging may be extended, for example, in a method in which a large size vessel is used for crystallization to extend the average retention time of slurry therein. The optimum aging time is selected from the viewpoint of the quality of the crystals, the economical efficiency of the process and the like.

In the present invention, the first slurry obtained in the crystallization step (i) having a desired slurry concentration is then subjected to a solid-liquid separation (step (ii)) to obtain the ε-caprolactam and a liquid phase (which is a first liquid phase).

The first liquid phase may be recycled and reused as a solvent for diluting the crude ε-caprolactam to be crystallized in step(i).

The separation of ε-caprolactam from the slurry may be carried out by any suitable known filtration method using, for example, a vacuum filter or a pressure filter. Alternatively, the separation may be conducted in sedimentation, centrifugal separation (using, for example, a conical conveyor discharge centrifuge) or decantation (using, for example, a centrifugal decanter), in which the separation can be continuously conducted. The conical conveyor discharge centrifuge or the centrifugal decanter is preferably utilized, since such a filter makes it possible to rinse the separated ε-caprolactam continuously and to wash off the impurities attached to the ε-caprolactam, so as to improve the quality of the ε-caprolactam. For the rinsing, the same kind of solvent comprising an aliphatic hydrocarbon as utilized in the crystallization step may be used.

In accordance with the present invention which comprises the crystallization step (i) and the solid-liquid separation step (ii), an ε-caprolactam having less than 10 ppm of cyclohexanone oxime, less than 10 ppm of OHP and less than 25 ppm of MTHI based on an ε-caprolactam may be obtained.

In the present invention, ε-caprolactam having a very high quality as described above, may be obtained in the process in which the crystallization is conducted only once (in step (i)), followed by the separation (in step(ii)) (1-stage crystallization method).

The process may further comprise, between step (i) and step (ii), the steps of:

(iii) separating a portion of a liquid phase from the first slurry containing the crystallized ε-caprolactam obtained in step(i) (using, for example, a hydrocyclone) to obtain a liquid phase (second liquid phase) and a remaining slurry (second slurry) containing the crystallized ε-caprolactam and (iv) adding a solvent comprising an aliphatic hydrocarbon and having a lower temperature than that of the second slurry into the second slurry to crystallize ε-caprolactam, to obtain a third slurry containing the crystallized ε-caprolactam (2-stage crystallization method). The second slurry obtained in step (iv) in the 2-stage crystallization method may be followed by the solid-liquid separation in step (ii) to provide ε-caprolactam having a much higher quality in a high yield. Especially, the 2-stage crystallization method has advantages such that the amount of the impurities (such as OHP) attached to and contained in the obtained ε-caprolactam is reduced. The second slurry obtained in step (iii) may be sent back to the vessel for crystallization in step (i). In this case, the required performance of the solid-liquid separator can be improved while maintaining the same ε-caprolactam yield.

The degree of removal of impurities from ε-caprolactam can be controlled in the crystallization step by adjusting the conditions thereof such as the kind and/or the amount of the solvent to be used or the temperature. Appropriate conditions can be selected by preliminary experiments. The crystallization may be carried out one or more times, while it is recommended to repeat the crystallization two or more times when the crude ε-caprolactam contains large amount of impurities. Caprenolactams, which may be difficult to remove in a one step crystallization, can be removed from ε-caprolactam in another treatment in which the ε-caprolactam obtained after the crystallization is allowed to contact with hydrogen in the presence of a hydrogenation catalyst. By such a treatment, the amount of caprenolactams in ε-caprolactam can be reduced to 25 ppm or less based on the ε-caprolactam.

The liquid phase obtained after the solid-liquid separation step (ii) may be subjected to other treatment(s) such as distillation, extraction, chemical treatment, active carbon treatment or a combination thereof, to purify and recover the ε-caprolactam contained therein. Alternatively, the liquid phase may be treated again by crystallization to obtain crude ε-caprolactam, which is then sent back, recycled and reused as crude ε-caprolactam in the crystallization step (i). In such a recycle process, ε-caprolactam contained in the liquid phase can be efficiently recovered as a high purity ε-caprolactam.

Specifically, the recycle process may be conducted by the steps of crystallizing the ε-caprolactam in the first liquid phase obtained in a 1-stage or 2-stage crystallization method, in the second liquid phase obtained in a 2-stage crystallization method and/or in a filtrate obtained in a washing step of a crystallized ε-caprolactam to recover crude ε-caprolactam and then recycling and reusing the crude ε-caprolactam as a crude ε-caprolactam in the crystallization step (i). This recycle process economically provides an ε-caprolactam in a high yield. The crystallization using the above-described liquid phase or the like (which contains a solvent comprising an aliphatic hydrocarbon as well as ε-caprolactam) may be conducted in a way such that the liquid phase or the like is preferably concentrated at a constant temperature while being heated and being evaporated (which is so-called "an evaporation crystallization method"). Evaporation crystallization method is advantageous from the standpoint of decreasing scale generation. From the standpoint of reducing energy consumption, it is advantageous to remove the solvent at some extent from the liquid phase or the like using a multiple effect evaporator or the like, before carrying out the evaporation crystallization method. The remaining liquid portion obtained after the evaporation crystallization may be exhausted out of the system of the process as it is or after being condensed to remove the solvent therefrom, thereby accumulation of impurities in the system is avoided to make it possible to conduct a continuous process for producing ε-caprolactam for a long period of time.

Referring now to FIG. 1, an embodiment of the process of the present invention, which is a process for continuously producing ε-caprolactam, is described as follows. In FIG. 1, the reference numerals 1, 3 and 7 all represent crystallization vessels, 2, 4 and 8 represent solid-liquid separation apparatus, 5 represents an apparatus for washing crystals, 6 represents a dissolving vessel, 9 represents a cooling apparatus and the numbers ranging from 10 to 16 represent lines.

Molten crude ε-caprolactam, which is prepared in dissolving vessel 6, is supplied through line 10 to crystallization vessel 1. At the same time, a solvent cooled in cooling apparatus 9 is supplied through line 11 to the crystallization vessel 1. In preparing the molten crude ε-caprolactam in dissolving vessel 6, a solvent comprising an aliphatic hydrocarbon may be used. In this case, ε-caprolactam crystals having a small amount of cyclohexanon oxime tends to be obtained compared with the case in that such a solvent is not used in the dissolving vessel 6.

The process steps carried out in the crystallization vessel 1, the solid-liquid separation apparatus 4, the apparatus 5 for washing crystals and the lines therebetween are conducted under conditions where a temperature of the slurry therein is maintained and does not fall, and each may be heated or cooled, if necessary. The crystallization in the crystallization vessel 1 is preferably carried out at a temperature of from about 30° C. to about 60° C. The temperature in the crystallization vessel 1 may be adjusted by controlling amount of the molten crude ε-caprolactam supplied from dissolving vessel 6 and the amount and temperature of the solvent supplied from the cooling apparatus 9.

In the crystallization vessel 1, a slurry (first slurry) containing crystallized ε-caprolactam is obtained. The slurry is supplied through line 12 to separation apparatus 4. Separation apparatus 4 may be a centrifugal filter or a centrifugal decanter. Of course, other suitable separation apparatus for use in the present invention will be apparent to one skilled in the art. The slurry supplied thereto is separated into a solid phase (which comprises crystallized ε-caprolactam) and a liquid phase (first liquid phase)(which comprises the solvent having an aliphatic hydrocarbon and impurities dissolved therein). The separated ε-caprolactam crystals may be supplied to apparatus 5 for washing crystals and be washed with a solvent comprising an aliphatic hydrocarbon so as to wash away the impurities attached to the surface of the ε-caprolactam crystals. Although it is not an essential feature of the invention, as the result of the washing, an ε-caprolactam having a higher purity is obtained than that obtained without the washing.

Before being supplied to the separation apparatus 4, a part or all of the slurry containing the crystallized ε-caprolactam obtained in the crystallization vessel 1 may be supplied to the separation apparatus 2 to separate a portion (second liquid phase) of the solvent comprising an aliphatic hydrocarbon and then be supplied to the crystallization vessel 3 to conduct crystallization again. In this case, purified ε-caprolactam is obtained in a higher yield than that obtained without such a re-crystallization. The portion of the solvent separated from the slurry in the separation apparatus 2 is not limited and may be from 10% to 70% of the liquid phase. The crystallization method employed in the crystallization vessel 3 may be the same method as in crystallization vessel 1. For example, the crystallization in the crystallization vessel 3 may be conducted so that the slurry obtained in the separation apparatus 2 and a solvent comprising an aliphatic hydrocarbon are preferably poured at the same time into the crystallization vessel 3 and are mixed with each other to obtain a slurry (third slurry) contained ε-caprolactam crystallized therein, while maintaining the temperature of the inner surface of crystallization vessel 3 at the same (or a little bit higher) temperature as (or than) the crystallization temperature described above. The crystallization temperature in the crystallization vessel 3 is preferably of from about 30° C. to about 60° C. and may be lower than that in the crystallization vessel 1. The slurry (third slurry) obtained in crystallization vessel 3 is then supplied through line 13 to separation apparatus 4 and is treated in the same manner as described above.

The liquid phase separated in separation apparatus 2, the liquid phase separated in separation apparatus 4 and a liquid phase exhausted from apparatus 5 for washing crystals comprise the solvent comprising an aliphatic hydrocarbon, and a portion thereof may be used as a solvent in dissolving vessel 6. The remaining portion thereof, which is not used in dissolving vessel 6, is sent through line 15 to crystallization vessel 7 in which crude ε-caprolactam contained in the remaining portion is crystallized. The crystallization conducted in crystallization vessel 7 may be any suitable type of crystallization method with evaporation crystallization method being preferably conducted. When evaporation crystallization is conducted in crystallization vessel 7, solvent exhausted from vessel 7 (a line for which is not illustrated in FIG. 1) is a purified solvent (since the solvent is recovered by evaporation). This purified solvent can be reused as a solvent in crystallization vessel(s) 1 and/or 3 and/or as a solvent for washing crystals in apparatus 5.

Slurry containing crude ε-caprolactam obtained in crystallization vessel 7 is then supplied through line 16 to separation apparatus 8 for separation into a solid phase (which comprises crude crystallized ε-caprolactam) and a liquid phase (which comprises solvent having an aliphatic hydrocarbon and impurities concentrated therein). Crude ε-caprolactam obtained in separation apparatus 8 may be sent via dissolving vessel 6 to crystallization vessel 1 to be treated therein and recovered as purified ε-caprolactam. On the other hand, the liquid phase exhausted from separation apparatus 8 may be sent into a solvent-recovering step (not illustrated), in which the liquid phase may be distilled and be separated into the solvent and impurities as a residue. When the solvent used for crystallization is a mixture of solvents having different boiling points from each other, the mixed solvent recovered after the distillation may be preferably reused after adjusting the mixing ratio thereof to the desirable ratio, since the mixing ratio of the recovered solvent may differ from the ratio of the solvent which has been utilized in the crystallization. In the process of the present invention, recovered solvent can be recycled and reused as a solvent in crystallization vessel 1 and the like, and the process only produces waste in the form of residue in the solvent-recovering step. As described above, the present invention provides an environmentally friendly process for producing ε-caprolactam, which produces little waste. In addition, the present invention provides a process for purifying ε-caprolactam, which is conducted continuously in an industrial scale in an efficient and economical way.

In accordance with the present invention, crude ε-caprolactam (such as ε-caprolactam having about 10 or more of a potassium permanganate value (PM value; as defined above), which is an indicator of the amount of impurities, about 10 ppm or more of cyclohexanone oxime, about 10 ppm or more of OHP and/or about 25 ppm or more of MTHI) is purified with crystallization usually only once even in a continuous manner, to obtain a high quality ε-caprolactam (such as an ε-caprolactam having less than about 10 ppm of cyclohexanone oxime, less than about 10 ppm of OHP and less than about 25 ppm of MTHI. The obtained ε-caprolactam may be subjected to a hydrogenation, a permanganate treatment or the like to provide a product ε-caprolactam that can be practically utilized as a raw material for the manufacture of polyamides such as Nylon-6.

EXAMPLES

The present invention is illustrated by the following Examples, which do not limit the scope of the invention in any way.

The following measurement techniques were used in the Examples to evaluate the qualities of the obtained ε-caprolactam: Purity of ε-caprolactam and content of impurities therein:

Purity of ε-caprolactam and content of impurities therein are obtained as follows (unless noted otherwise):

A sample ε-caprolactam was analyzed with gas chromatography (GC) using a capillary column (DB-WAX; 30 m). In the obtained GC chromatogram, a percentage area of ε-caprolactam and a percentage area of each impurity are respectively calculated based on the total area subtracting those of the solvent and impurities of the solvent, and are used as a purity of the ε-caprolactam and the content of each impurity (except for OHP) contained in ε-caprolactam. The limit of detection of impurities (except for OHP) was about 3 ppm.

Separately, a sample ε-caprolactam was analyzed with liquid chromatography (LC) using a column (ODS; 15 cm), water-acetonitrile as a carrier solvent and an UV detector in a gradient method. Using the obtained LC chromatogram, the content of OHP contained in the ε-caprolactam is calculated with an absolute working curve method. The limit of detection of OHP was about 0.1 ppm.

Ultraviolet Ray Transmittance (UV Transmittance)

A sample ε-caprolactam (1.13 g) was dissolved in water to make 10 ml of the solution, and then an ultraviolet ray (UV) transmittance through the solution at a wavelength of 290 nm or 315 nm was measured using a 10-mm quartz cell and water as a reference solution. Separately, An aqueous solution (50%) of the ε-caprolactam was prepared. An UV transmittance of the aqueous solution was measured in the same manner as described above, and referred to as an UV transmittance of 50% ε-caprolactam aqueous solution.

Potassium Permanganate Value (PM Value)

A sample ε-caprolactam (1 g) was dissolved in distilled water to make 100 ml of the solution. To this solution, a 0.01 N aqueous solution of potassium permanganate (2 ml) was added and the resulting solution was stirred. After 250 seconds from the addition of the solution of potassium permanganate, the absorbance of the resulting solution was measured with a light having a wavelength of 420 nm at 25° C. (of a temperature of the solution).

Separately, a solution consisting of distilled water and the aqueous solution of potassium permanganate was prepared as a reference solution and the absorbance thereof was measured with light having a wavelength of 420 nm at 25° C. (of a temperature of the solution).

The latter absorbance (of the solution of potassium permanganate) was subtracted from the former absorbance (of the solution of ε-caprolactam) and the obtained value was multiplied by 100 to obtain the potassium permanganate (PM) value of the ε-caprolactam.

Free Basicity (FB)

Distilled water was adjusted to have a pH of 5.7 by the addition of 0.01 N sulfuric acid or 0.01 N aqueous sodium hydroxide. To such distilled water (40 ml), a sample ε-caprolactam (10 g) was added and the resulting solution was stirred. Then, pH of the resulting solution was measured. If the pH thereof is larger than 5.7, 0.01 N sulfuric acid was added to the solution until the pH reaches 5.7.

A free basicity (meq/kg) of the ε-caprolactam was calculated from the consumed amount (v:ml) of 0.01 N sulfuric acid, the factor (f) of sulfuric acid, and the weight (w:g) of the ε-caprolactam, based on the following equation:

$$FB \text{ (meq/kg)} = \{0.01 \times v(\text{ml}) \times f \times 1000\}/w(g)$$

pH Value

Distilled water was adjusted to have a pH of 5.7 by the addition of a dilute sulfuric acid or a dilute aqueous sodium hydroxide. To such distilled water (1 ml), a sample ε-caprolactam (0.25 g) was added and the resulting solution was stirred. Then, the pH of the resulting solution was measured to obtain a pH of the ε-caprolactam.

Example 1

A continuous process for producing ε-caprolactam was carried out as follows. The flow amount of liquid is described with parts by weight per unit time (unless noted otherwise).

Using a fluidized bed reactor packed with a high silica zeolite catalyst, a gaseous phase Beckmann rearrangement reaction of cyclohexanone oxime (hereinafter, referred to as "OXM") was conducted in the presence of methanol at 380° C. to obtain a reaction mixture containing crude ε-caprolactam.

This reaction mixture was distilled to remove methanol, low-boiling impurities and high-boiling impurities to obtain crude ε-caprolactam having a purity of 99.131%, which contained 139 ppm of OXM, 398 ppm of MTHI and 430 ppm of OHP.

Into a crystallization vessel having a jacket for maintaining a temperature of 56° C., were continuously poured the obtained crude ε-caprolactam (200 parts by weight; at 75° C.) which had been obtained as above and had been previously molten, and a mixed solvent of cyclohexane and n-heptane (weight ratio of 1:3) (400 parts by weight; at 5° C.). The temperature of the crystallization vessel was maintained at 55° C. and the retention time was about 30 minutes, to crystallize ε-caprolactam and obtain a slurry containing precipitated ε-caprolactam. The slurry (600 parts by weight) was sent from the crystallization vessel to a centrifugal decanter (maintaining its temperature) to conduct a solid-liquid separation. The obtained solid phase was continuously washed with the above-identified mixed solvent containing the same components in the same ratio (80 parts by weight; at about 50° C.), to obtain crystalline ε-caprolactam (150 parts by weight) and a liquid phase (530 parts by weight). The obtained crystalline ε-caprolactam was analyzed as described above. Purity of the ε-caprolactam was 99.99%, with the contents of OXM, MTHI and OHP all being less than the limit of detection, and the content of caprenolactams being 114 ppm. It is noted that, based on the obtained crystalline ε-caprolactam (without the solvents), the content of ε-caprolactam was 96.33% by weight, the content of n-heptane was 2.06% by weight and the content of cyclohexane was 1.26% by weight. The above coutinuous process was conducted stably for more than 24 hours.

Reference Example 1

A hydrogenation catalyst (2% palladium/activated carbon catalyst) (4.0 g) was filled in a tube having an inner diameter of 6 mm. The height of the catalyst layer was 9.5 cm. The crystalline ε-caprolactam obtained in Example 1 was molten and was fed at 80° C. into the tube reactor at a rate of 0.34 cc/min., while allowing a hydrogen gas to flow at a flow rate of 6 cc/min. under a hydrogen pressure of 5 kg/cm$^2$ (about 0.5 MPa), to conduct a hydrogenation reaction of caprenolactams. After adding sodium hydroxide (0.028% by weight), the resulting ε-caprolactam was subjected to distillation under a reduced pressure. The obtained ε-caprolactam was analyzed as described above. As a result, the purity of ε-caprolactam was 99.997%, the contents of OXM, MTHI, OHP and caprenolactams were all less than the limit of detection, the PM value was 1.4, the FB was 0.057 meq/kg, UV transmittances of 50% aqueous solution of the ε-caprolactam at 290 nm and 315 nm were 95.0% and 98.3%, respectively. The obtained ε-caprolactam was found to have a high quality sufficient to be used as an industrial product ε-caprolactam.

Comparative Example 1

A continuous process for producing ε-caprolactam was carried out as follows. The flow amount of liquid is described with parts by weight per unit time (unless noted otherwise).

In the same manner as described in Example 1, cyclohexanone oxime (OXM) was subjected to the Beckmann rearrangement and the obtained crude ε-caprolactam was distilled to remove methanol, low-boiling impurities and high-boiling impurities, to obtain a crude ε-caprolactam having a purity of 99.334%, which contained 149 ppm of OXM, 114 ppm of MTHI and 482 ppm of OHP.

Into a crystallization vessel having a jacket for maintaining the temperature of 65° C., was poured the obtained crude ε-caprolactam (200 parts by weight) and then was poured a mixed solvent of cyclohexane and n-heptane (weight ratio of 1:3) (400 parts by weight). The jacket of the crystallization vessel was cooled from at 65° C. to at 56° C. over 30 minutes and was maintained at 56° C., to crystallize ε-caprolactam and obtain a slurry containing the crystallized ε-caprolactam. The slurry was sent from the crystallization vessel to a centrifugal filter (maintaining its temperature at 56° C.) to conduct a solid-liquid separation. The obtained solid phase was washed continuously with the above-identified mixed solvent containing the same components in the same ratio (80 parts by weight; at about 50° C.), to obtain a crystalline ε-caprolactam (122 parts by weight) and a liquid phase. The obtained crystalline ε-caprolactam was analyzed as described above. Purity of the ε-caprolactam was 99.98%, the contents of OXM, MTHI and OHP were all less than the limit of detection, and the content of caprenolactams was 173 ppm.

In the crystallization vessel, remained 33 parts by weight of ε-caprolactam scales, which was not able to be exhausted. The liquid phase (obtained from the solid-liquid separation and the washing step) and the crystalline scales attached to the vessel were put together. From the resulting mixture, was removed a solvent contained therein under reduced pressure to obtain a crude ε-caprolactam (44 parts by weight). The obtained ε-caprolactam was analyzed as described above. As a result, the purity of ε-caprolactam was 99.98%, the contents of OXM, MTHI and OHP were all less than the limit of detection and the content of caprenolactams being 173 ppm.

Example 2

Into a fluidized bed reactor packed with a high silica zeolite catalyst, a liquid mixture of OXM, methanol and water (weight ratio of 1:1.8:0.052) was introduced together with a nitrogen gas through a vaporizer, and was subjected to a Beckmann rearrangement reaction of OXM under the condition of a reaction temperature of 380° C. and a retention time of 8 seconds, to obtain a reaction mixture containing crude ε-caprolactam.

This reaction mixture was distilled to remove methanol, low-boiling impurities and high-boiling impurities to obtain a crude ε-caprolactam having a purity of 99.08%, which contained 188 ppm of OXM, 469 ppm of MTHI and 205 ppm of OHP.

A mixture of the obtained crude ε-caprolactam (55 g) and n-heptane (82.5 g) was prepared and was maintained at 70°

C. Separately, n-heptane (41.25 g) was cooled with ice. Into a flask charged with another n-heptane (41.25 g) at 58° C., were continuously poured together (over 10 minutes) the mixture of the crude ε-caprolactam and n-heptane and the cooled n-heptane, to crystallize ε-caprolactam and obtain a slurry containing the crystallized ε-caprolactam. After 30 minutes, the slurry was filtered with a centrifugal-type filter. The obtained solid phase was washed with the n-heptane (27.5 g) while being maintained at 58° C., to obtain crystalline ε-caprolactam. After vacuum drying, the crystalline ε-caprolactam was measured and analyzed. The yield of ε-caprolactam was 63.2%. Purity of the ε-caprolactam was 99.98%, with the content of OXM being 1 ppm, the contents of MTHI. and OHP being less than the limit of detection and the content of caprenolactams being 173 ppm.

Reference Example 2

The crystalline ε-caprolactam obtained in Example 2 was molten in the atmosphere of nitrogen gas. The molten ε-caprolactam (28 g) was fed into the tube reactor packed with a hydrogenation catalyst (granule; 2% palladium/activated carbon catalyst) (0.9 g) at a WHSV of from 5.3 to 6.6 /h., while allowing a hydrogen gas to flow at a flow rate of 3 cc/min. under a hydrogen pressure of 5 kg/cm$^2$ (about 0.5 MPa), to conduct a hydrogenation reaction of the ε-caprolactam. The resulting ε-caprolactam discharged from the tube reactor was subjected to distillation under a reduced pressure, to obtain purified ε-caprolactam (25.5 g). The obtained ε-caprolactam was analyzed as described above. Purity of the ε-caprolactam was 99.99%, the contents of OXM, MTHI and OHP were all less than the limit of detection, the content of caprenolactams was 14 ppm, UV transmittances of 50% aqueous solution of the ε-caprolactam at 290 nm and 315 nm were 98.2% and 99.0%, respectively, the PM value was 4.4, the pH value was 5.99 and the FB was 0.065 meq/kg. The obtained ε-caprolactam was found to have a high quality sufficient to be used as an industrial product ε-caprolactam Example 3

In the same manner as described in Example 2, cyclohexanone oxime (OXM) was subjected to the Beckmann rearrangement and the obtained crude ε-caprolactam was distilled, to obtain crude ε-caprolactam having a purity of 98.32%, which contained 1542 ppm of OXM, 775 ppm of MTHI, and 423 ppm of OHP.

In a 500 ml flask, the obtained crude ε-caprolactam (66 g) was dissolved with a mixed solvent of toluene and isooctane (weight ratio of 9.7:90.3) (101.3 g) at 65° C. Separately, the same kind of mixed solvent (41.25 g) was prepared in a dropping funnel and was cooled with ice.

Into a flask charged with the same kind of another mixed solvent (41.25 g) at 52° C., were concurrently dropwise added over 10 minutes the mixture (at 65° C.) of ε-caprolactam and the ice-cooled mixed solvent, to crystallize ε-caprolactam while stirring. After the mixture was stirred for 20 minutes at 300 rpm, the resulting mixture was filtered with a centrifugal separator maintained at 52° C. to obtain the crystalline ε-caprolactam. The crystalline ε-caprolactam was then washed with the above-identified mixed solvent containing the same components in the same ratio (27.5 g, 52° C.). The obtained ε-caprolactam was dried under reduced pressure to obtain crystalline ε-caprolactam (42.18 g). The obtained crystalline ε-caprolactam was analyzed as described above. Purity of the ε-caprolactam was 99.979%, the content of OXM was 4.7 ppm, the contents of MTHI and OHP were less than the limit of detection, the content of caprenolactams was 184 ppm, the PM value was 50.9, the FB was 0.030 meq/kg and the pH value was 5.95.

Reference Example 3

The crystalline ε-caprolactam obtained in Example 3 was molten at 80° C. under a nitrogen atmosphere. The crystalline ε-caprolactam (35 g) was fed into a catalyst layer packed with a hydrogenation catalyst (granule; 2%Pd/activated carbon catalyst) (0.9 g) at a space velocity WHSV of 5 h$^{-1}$ while allowing a hydrogen gas to flow at a flow rate of 3 cc/min. under a hydrogen pressure of 5 kg/cm$^2$ (about 0.5 MPa), to conduct a hydrogenation reaction of the ε-caprolactam. The resulting ε-caprolactam was analyzed as described above. Purity of the ε-caprolactam was 99.997%, the content of OXM was 2 ppm, the contents of MTHI and OHP were all less than the limit of detection, the content of caprenolactams was 9 ppm, UV transmittances of 50% aqueous solution of the ε-caprolactam at 290 nm and 315 nm were 97.6% and 98.2%, respectively, the PM value was 1.3, the FB was 0.021 meq/kg, and the pH value was 5.85. The obtained ε-caprolactam was found to have a high quality sufficient to be used as an industrial product ε-caprolactam.

Example 4

In the same manner as in Example 2, cyclohexanone oxime (OXM) was subjected to the Beckmann rearrangement and the obtained crude ε-caprolactam was distilled to obtain a crude ε-caprolactam having a purity of 99.582%, which contained 123 ppm of OXM, 106 ppm of MTHI and 453 ppm of OHP.

The obtained crude ε-caprolactam (200 g) was dissolved in a mixed solvent of ethyl acetate and n-heptane (weight ratio of 1:57) (100 g) at 65° C. and was put in a dropping funnel. Separately, the above-identified mixed solvent containing the same components in the same ratio (100 g) was prepared in another dropping funnel and was maintained at about 0° C.

Into a 1 L flask charged with the same kind of another mixed solvent (100 g), were concurrently dropwise added at 52° C. over 10 minutes the mixture (at 65° C.) of ε-caprolactam and the cooled mixed solvent (at about 0° C.), to crystallize ε-caprolactam while stirring. After the mixture was stirred for 20 minutes at 300 rpm, the resulting mixture was filtered with a centrifugal filter maintained at 52° C., to obtain the crystallized ε-caprolactam. The obtained ε-caprolactam was washed with the above-identified mixed solvent containing the same components in the same ratio (100 g; 52° C.) and was dried under reduced pressure to obtain a crystalline ε-caprolactam (168.8 g). The obtained crystalline ε-caprolactam was analyzed as described above. As a result, the purity of ε-caprolactam was 99.977%, the content of OXM was 1 ppm, the contents of MTHI and OHP were less than the limit of detection, the content of caprenolactams was 218 ppm.

Example 5

In the same manner as in Example 2, cyclohexanone oxime (OXM) was subjected to the Beckmann rearrangement and the obtained crude ε-caprolactam was distilled to obtain a crude ε-caprolactam having a purity of 98.993%, which contained 1100 ppm of OXM, 433 ppm of MTHI and 208 ppm of OHP.

The obtained crude ε-caprolactam (55.05 g) was dissolved in a mixed solvent of cyclohexane and n-heptane (weight ratio of 1:3) (82.5 g) at 60° C. and was put in a dropping funnel while maintaining a temperature of 60° C. Separately, the above-identified mixed solvent containing the same components in the same ratio (41.25 g) was prepared in another dropping funnel and was maintained at about 5° C.

Into a flask charged with the same kind of another mixed solvent (41.25 g), were concurrently dropwise added at 50° C. over 10 minutes the mixture (at 65° C.) of ε-caprolactam and the mixed solvent (at about 5° C.) while stirring at 350 rpm. After 2 minutes, a slight amount of ε-caprolactam crystal was added to the mixture as a seed crystal. The mixture was stirred for 30 minutes, and the resulting mixture was filtrated with a centrifugal filter while maintaining a temperature of 50° C., to obtain ε-caprolactam crystals. The ε-caprolactam was washed with the above-identified mixed solvent containing the same components in the same ratio (27.5 g) and was dried under reduced pressure to obtain a crystalline ε-caprolactam (42.95 g). The obtained crystalline ε-caprolactam was analyzed as described above. As a result, the purity of ε-caprolactam was 99.980%, the content of OXM was 7.4 ppm, the contents of MTHI and OHP were less than the limit of detection, the content of caprenolactams was 165 ppm, the PM value was 51, and the FB was 0.033 meq/kg.

Reference Example 4

Crystalline ε-caprolactam (35.00 g) obtained in Example 5 was dissolved in a mixed solvent of cyclohexane and n-heptane (weight ratio of 1:3) (52.5 g), and the resulting solution was put in a dropping funnel while maintaining a temperature of 60° C. Separately, a mixed solvent of cyclohexane and n-heptane (weight ratio of 1:3) (26.25 g) was prepared in a dropping funnel while maintaining a temperature of about 5° C.

Into a flask charged with the same kind of another mixed solvent (26.25 g), were concurrently dropwise added at 50° C. over 10 minutes the mixture of ε-caprolactam and the mixed solvent (at about 60° C.) and another mixed solvent (at 5° C.) while stirring at 350 rpm. After 2 minutes, a slight amount of ε-caprolactam crystal was added to the mixture as a seed crystal, to crystallize ε-caprolactam. After the mixture was stirred for 30 minutes, the resulting mixture was filtered with a centrifugal filter at 50° C. The ε-caprolactam was washed with the above-identified mixed solvent containing the same components in the same ratio (27.5 g) and was dried under reduced pressure to obtain a crystalline ε-caprolactam (22.55 g). The obtained crystalline ε-caprolactam was analyzed as described above. Purity of ε-caprolactam was 99.986%, the content of OXM was 4.1 ppm, the contents of MTHI and OHP were less than the limit of detection, the content of caprenolactams was 84 ppm, the PM value was 24.7 and the FB was 0.031 meq/kg.

Example 6

Crude ε-caprolactam (200 g) having an OHP content of 2270 ppm was dissolved in a mixed solvent of cyclohexane and n-heptane (weight ratio of 1:3) (100 g) at 65° C., and was put in a dropping funnel. Separately, the above-identified mixed solvent containing the same components in the same ratio (100 g, at about 0° C.) was charged in another dropping funnel.

Separately, the above-identified mixed solvent containing the same components in the same ratio (100 g) was poured in a crystallization vessel. Into the vessel, the mixture of the ε-caprolactam (at about 65° C.) and the mixed solvent (at about 0° C.) were concurrently dropwise added at 55° C. over 10 minutes while stirring at 250 rpm. After stirring for 20 minutes at 55° C., the resulting mixture was subjected to a solid-liquid separation with a centrifugal filter while maintaining a temperature of 55° C., to obtain the crystalline ε-caprolactam and a liquid phase. The ε-caprolactam was washed with the above-identified mixed solvent containing the same components in the same ratio (100 g; 55° C.) and was dried to obtain a crystalline ε-caprolactam (168.2 g). The obtained crystalline ε-caprolactam was analyzed as described above. As a result, the ε-caprolactam had an OHP content of 2 ppm. The liquid phase obtained after the solid-liquid separation and the liquid phase obtained in the washing step were put together and were condensed to remove the solvent therein. As a result, crude ε-caprolactam (31.03 g) was obtained. The crude ε-caprolactam had an OHP content of 14,300 ppm.

Example 7

In the same manner as in Example 2, cyclohexanone oxime (OXM) was subjected to the Beckmann rearrangement and the obtained crude ε-caprolactam was distilled to obtain crude ε-caprolactam. Into the crude ε-caprolactam, was added cyclohexanone oxime (OXM) to prepare a crude ε-caprolactam to be crystallized. The prepared crude ε-caprolactam had a purity of 99.005%, which contained 1002 ppm of OXM, 448 ppm of MTHI and 246 ppm of OHP.

The crude ε-caprolactam (110 g) thus prepared was put in a dropping funnel and was molten at 70° C. Separately, a mixed solvent of cyclohexane and n-heptane (weight ratio of 1:3) (123.8 g) was prepared in another dropping funnel and was cooled with ice.

Separately, the above-identified mixed solvent containing the same components in the same ratio (41.2 g) was poured in a flask. Into the flask, the molten ε-caprolactam and the ice-cooled mixed solvent were concurrently dropwise added at 52° C. over 10 minutes while stirring at 350 rpm. After stirring for 30 minutes at 52° C., the resulting mixture was subjected to a solid-liquid separation with a centrifugal filter keeping a temperature of 52° C., to obtain the crystallized ε-caprolactam and a liquid phase. The ε-caprolactam was washed with the above-identified mixed solvent containing the same components in the same ratio (55 g; 52° C.) and was dried under reduced pressure to obtain a crystalline ε-caprolactam (88.78 g). The obtained crystalline ε-caprolactam was analyzed as described above. Purity of the ε-caprolactam was 99.963%, the content of OXM was 22 ppm, the contents of MTHI and OHP were less than the limit of detection and the content of caprenolactams was 228 ppm.

Example 8

Into the liquid phase obtained after the solid-liquid separation and the liquid phase obtained after the washing, which had been obtained in Example 7, was added and dissolved the ε-caprolactam which had been prepared in the same manner as in Example 7. The resulting mixture was put in a dropping funnel. The mixture had an OXM content of 1600 ppm. Separately, the above-identified mixed solvent containing the same components in the same ratio (123.8 g) was put in another dropping funnel and was cooled with ice.

Separately, the above-identified mixed solvent containing the same components in the same ratio (41.2 g) was poured in a flask. Into the flask, the dissolved ε-caprolactam and the cooled mixed solvent were concurrently dropwise added at 52° C. over 10 minutes while stirring at 350 rpm. After stirring for 30 minutes at 52° C., the resulting mixture was filtered with a centrifugal filter while maintaining a temperature of 52° C., to obtain the precipitated ε-caprolactam. The ε-caprolactam was washed with the above-identified mixed solvent containing the same components in the same ratio (52° C.) and was dried under reduced pressure to obtain crystalline ε-caprolactam (90.49 g). The obtained crystalline ε-caprolactam was analyzed as described above. Purity of ε-caprolactam was 99.9743%, the content of OXM was 5 ppm, the contents of MTHI and OHP were less than the limit of detection and the content of caprenolactams was 218 ppm.

Example 9
(1-Stage crystallization method)

A continuous process for producing ε-caprolactam was carried out as follows. The flow amount of liquid is described with parts by weight per unit time (unless noted otherwise).

Using a zeolite catalyst, a Beckmann rearrangement reaction of OXM was conducted in the presence of methanol to obtain a reaction mixture containing crude ε-caprolactam.

This reaction mixture was distilled to remove methanol, low-boiling impurities and high-boiling impurities to obtain a crude ε-caprolactam having a purity of 99.20%, which contained 496 ppm of OXM, 181 ppm of MTHI and 242 ppm of OHP. The crude ε-caprolactam contained a mixed solvent of cyclohexane and n-heptane (weight ratio of 1:3.86) in which the mixed solvent content was 1.70% in the crude ε-caprolactam.

Into a crystallization vessel having a jacket for maintaining a temperature of 56° C., were continuously poured the crude ε-caprolactam (300 parts by weight; at 73° C.), which had been obtained as above and had been previously molten, and a mixed solvent of cyclohexane and n-heptane (weight ratio of 1:3) (550 parts by weight; at 5.5° C.). The temperature of the crystallization vessel was maintained at 56° C., to crystallize ε-caprolactam and obtain a slurry containing the crystallized ε-caprolactam. The slurry was sent, while stirring, from the crystallization vessel to a centrifugal decanter (while maintaining its temperature) to conduct a solid-liquid separation so that the retention time of the slurry in the vessel was maintained at about 34 minutes. The obtained solid phase was continuously washed with the above-identified mixed solvent containing the same components in the same ratio (120 parts by weight; at about 50° C.), to obtain a crystalline ε-caprolactam (207 parts by weight) and a liquid phase (763 parts by weight). After removing the solvents, the obtained crystalline ε-caprolactam was analyzed as described above. Purity of the ε-caprolactam was 99.98%, the content of OXM was 6 ppm, the content of MTHI was less than the limit of detection, the content of OHP was 0.48 ppm and the content of caprenolactams was 172 ppm. The ε-caprolactam contained a mixed solvent of cyclohexane and n-heptane (weight ratio of 1:1.75) in which the mixed solvent content was 3.08% based on the ε-caprolactam. The above continuous process was conducted stably for more than 24 hours.

Example 10
(2-Stage Crystallization Method)

A continuous process for producing ε-caprolactam was carried out as follows. The flow amount of liquid is described with parts by weight per unit time (unless noted otherwise).

Using a zeolite catalyst, a Beckmann rearrangement reaction of OXM was conducted in the presence of methanol to obtain a reaction mixture containing crude ε-caprolactam.

This reaction mixture was distilled to remove methanol, low-boiling impurities and high-boiling impurities to obtain crude ε-caprolactam having a purity of 99.28%, which contained 509 ppm of OXM, 172 ppm of MTHI and 199 ppm of OHP. The crude ε-caprolactam contained a mixed solvent of cyclohexane and n-heptane (weight ratio of 1:3.67) in which the mixed solvent content was 1.23% based on the crude ε-caprolactam.

The obtained crude ε-caprolactam (300 parts by weight; at 73° C.), which had been previously molten, and a mixed solvent of cyclohexane and n-heptane (weight ratio of 1:3) (530 parts by weight; at 5° C.) were continuously poured into a first crystallization vessel having a jacket keeping at 56° C., to crystallize ε-caprolactam and obtain a first slurry containing the ε-caprolactam. While the ε-caprolactam was precipitated therein, the temperature of the slurry was 55.7° C. The slurry was sent, while stirring, from the first crystallization vessel to a hydrocyclone (maintaining its temperature) to conduct a solid-liquid separation so that the retention time of the slurry in the vessel was maintained at about 32 minutes, to obtain the liquid phase (230 parts) from the hydrocyclone.

The concentrated slurry (a second slurry) obtained from the hydrocyclone and the above-identified mixed solvent containing the same components in the same ratio (230 parts; at 9° C.) were continuously poured into a second crystallization vessel having a jacket for maintaining a temperature of 46.5° C., to crystallize ε-caprolactam and obtain a third slurry containing the ε-caprolactam. While the ε-caprolactam was precipitated therein, the temperature of the slurry was 46° C. The third slurry was sent from the crystallization vessel to a centrifugal decanter (while maintaining its temperature) to conduct a solid-liquid separation so that the retention time of the slurry was maintained at about 12.6 minutes in the vessel. The obtained solid phase was continuously washed with the above-identified mixed solvent containing the same components in the same ratio (120 parts by weight; at about 50° C.), to obtain crystalline ε-caprolactam (243 parts by weight) and a liquid phase (937 parts by weight). After removing the solvents, the obtained crystalline ε-caprolactam was analyzed as described above (after removing the solvents). Purity of the ε-caprolactam was 99.98%, the content of OXM was 4 ppm, the content of MTHI was 2 ppm, the content of OHP was 0.35 ppm and the content of caprenolactams was 181 ppm. The ε-caprolactam contained a mixed solvent of cyclohexane and n-heptane (weight ratio of 1:2.29) in which the mixed solvent content was 3.52% based on the ε-caprolactam. The above continuous process was conducted stably for more than 24 hours.

Example 11

A continuous process for producing ε-caprolactam was carried out as follows. The flow amount of liquid is described with parts by weight per unit time (unless noted otherwise).

A filtrate (ε-caprolactam 97.69%; OXM 1220 ppm; MTHI 451 ppm; OHP 849 ppm) was prepared. The filtrate contained the mixed solvent of cyclohexane and n-heptane (weight ratio of 1:2.75) in which the mixed solvent content was 86.35% based on the filtrate.

The filtrate (894 parts by weight) was distilled under pressure of 240 torr (about 0.032 MPa) at 58.5° C. to remove a mixed solvent (386 parts by weight) of cyclohexane and n-heptane.

The remaining filtrate and a liquid phase (230 parts by weight) were sent into a crystallization vessel under a pressure of 90 torr (about 0.012 MPa) at 40.6° C., and were distilled therein to crystallize ε-caprolactam and obtain a distillate, while adding a mixed solvent of cyclohexane and n-heptane (weight ratio of 1:3) (100 parts by weight) so that the solvent washed a part of the crystallization vessel surface with which a vapor phase in the vessel contacted. The obtained distillate was cooled and was recovered as a liquid phase (380 parts by weight). The average retention time in the crystallization vessel was 74 minutes. The resulting slurry (468 parts by weight) containing the crystallized ε-caprolactam was continuously sent out of the vessel to a centrifugal decanter (keeping its temperature of 40° C.) to conduct a solid-liquid separation. A crystalline ε-caprolactam (128 parts by weight) and a liquid phase (340 parts by weight) were obtained.

A portion (230 parts by weight) of the liquid phase was recycled and reused as a liquid phase to be mixed with the remaining filtrate described above. The remaining portion (100 parts by weight) of the liquid phase was sent to a solvent-recovering step and was distilled.

The crystalline ε-caprolactam thus obtained by the evaporation crystallization method was analyzed as described above (after removing the solvents). Purity of the ε-caprolactam was 99.68%, the content of OXM was 129 ppm, the content of MTHI was 69 ppm, the content of OHP was 25 ppm and the content of caprenolactams was 865 ppm. The ε-caprolactam contained a mixed solvent of cyclohexane and n-heptane (weight ratio of 1:3.98) in which the mixed solvent content was 8.59% based on the ε-caprolactam.

The ε-caprolactam was made molten and was continuously recycled and reused as a molten crude ε-caprolactam to be crystallized in the process of the present invention. With the above-described steps, the 116.6 parts by weight of ε-caprolactam was recycled from the 119.2 parts by weight of the ε-caprolactam contained in the filtrate prepared above.

The above coutinuous process was conducted stably for more than 24 hours.

The invention being thus described, it will be apparent that the same may be varied in many ways. Such variations are to be regarded as within the spirit and scope of the invention, and all such modifications as would be apparent to one skilled in the art are intended to be within the scope of the following claims.

What is claimed is:

1. A process for producing ε-caprolactam, comprising the steps of:
   (i) pouring molten, crude ε-caprolactam and a solvent together into a vessel, the solvent comprising an aliphatic hydrocarbon and having a temperature lower than the temperature of the crude ε-caprolactam, and mixing the ε-caprolactam and solvent at a temperature of from about 30° C. to less than the melting point of ε-caprolactam, to obtain a first slurry containing crystallized ε-caprolactam and
   (ii) subjecting the slurry to a solid-liquid separation to obtain the ε-caprolactam and a first liquid phase.

2. The process according to claim 1, wherein the molten, crude ε-caprolactam and the solvent are simultaneously poured together into the vessel.

3. The process according to claim 1, wherein the solvent comprising an aliphatic hydrocarbon contains an organic solvent having a higher polarity than that of the aliphatic hydrocarbon.

4. The process according to claim 1, wherein the molten crude ε-caprolactam contains a solvent comprising an aliphatic hydrocarbon.

5. The process according to claim 1, wherein the molten crude ε-caprolactam contains a solvent comprising an aliphatic hydrocarbon and an organic solvent having a higher polarity than that of the aliphatic hydrocarbon.

6. The process according to claim 1, wherein the aliphatic hydrocarbon is at least one hydrocarbon selected from the group consisting of linear aliphatic hydrocarbons having 6 to 12 carbon atoms, side chain aliphatic hydrocarbons having 6 to 12 carbon atoms and/or alicyclic hydrocarbons having 6 to 12 carbon atoms.

7. The process according to claim 1, wherein the aliphatic hydrocarbon is a combination of linear or chain aliphatic hydrocarbon with an alicyclic hydrocarbon.

8. The process according to claim 1, wherein the crystallization step (i) and the solid-liquid separation step (ii) are continuously conducted.

9. The process according to claim 1, wherein the crystallization step (i) is conducted under thermal insulation or with maintaining the crystallization temperature or under heating.

10. The process according to claim 1, wherein the total amount of solvent comprising an aliphatic hydrocarbon utilized for crystallization is within the range of from about 0.5 part by weight to about 5 parts by weight, based on the ε-caprolactam.

11. The process according to claim 1, further comprising, between step (i) and step (ii), the steps of:
   (iii) separating a portion of a liquid phase from the first slurry obtained in step (i) to obtain a second liquid phase and a second slurry containing the crystallized ε-caprolactam and
   (iv) adding a solvent into the second slurry to crystallize ε-caprolactam and obtain a third slurry containing the crystallized ε-caprolactam, the solvent added to the second slurry comprising an aliphatic hydrocarbon and having a temperature lower than the temperature of the second slurry.

12. The process according to claim 11, wherein the solvent comprising an aliphatic hydrocarbon added in the crystallization step (iv) contains an organic solvent having a polarity higher than the polarity of the aliphatic hydrocarbon.

13. The process according to claim 1, further comprising the step of:
   (vi) washing the ε-caprolactam obtained in the solid-liquid separation step (ii) with a solvent comprising an aliphatic hydrocarbon.

14. The process according claim 4, further comprising the step of:
   (vii) recycling an reusing in the crystallization step (i) a portion of a least one of the first liquid phase obtained in the solid-liquid separation step (ii) and/or the second liquid phase obtained in the separation step (iii) as the solvent comprising an aliphatic hydrocarbon and an organic solvent having a polarity higher than the polarity of the aliphatic hydrocarbon, which is contained in the molten crude ε-caprolactam.

15. The process according to claim 13, further comprising the step of:
   (vii)' recycling and reusing in the crystallization step (i) a portion of the liquid phase obtained after the washing step (vi) as the solvent comprising an aliphatic hydrocarbon or as the solvent comprising an aliphatic hydrocarbon and an organic solvent having a polarity higher than the polarity of the aliphatic hydrocarbon, which is contained in the molten crude ε-caprolactam.

16. The process according to claim 1, further comprising the steps of:
(viii) separating the solvent from a portion of a least one of the first liquid phase obtained in the solid-liquid separation step (ii) and/or the second liquid phase obtained in the separation step (iii), to obtain a slurry containing crystallized ε-caprolactam and
(ix) subjecting the slurry to a solid-liquid separation to obtain an crude ε-caprolactam and a third liquid phase.

17. The process according to claims 16, further comprising the steps of:
(viii)' separating the solvent from a portion or all of at least one of the first liquid phase obtained in the solid-liquid separation step (ii) and/or the second liquid phase obtained in the separation step (iii) and from a portion or all of the liquid phase obtained after the washing step (vi), to obtain a slurry containing crystallized ε-caprolactam, and
(ix)' subjecting the slurry to a solid-liquid separation to obtain an crude ε-caprolactam and a fourth liquid phase.

18. The process according to claims 16, further comprising the step of:
(x) recycling and reusing the crude ε-caprolactam obtained in the solid-liquid separation step (ix) as the crude ε-caprolactam utilized in the crystallization step (i).

19. The process according to claims 17, further comprising the step of:
(x)' recycling and reusing the crude ε-caprolactam obtained in the solid-liquid separation step (ix)' as the crude ε-caprolactam utilized in the crystallization step (i).

20. The process according to claims 16, further comprising the step of:
(xi) recovering the solvent comprising an aliphatic hydrocarbon from the third liquid phase obtained in the solid-liquid separation step (ix) and reusing the recovered solvent as the solvent comprising an aliphatic hydrocarbon in the crystallization step (i).

21. The process according to claims 17, further comprising the step of:
(xi)' recovering the solvent comprising an aliphatic hydrocarbon from the fourth liquid phase obtained in the solid-liquid separation step (ix)' and reusing the recovered solvent as the solvent comprising an aliphatic hydrocarbon in the crystallization step (i).

22. The process according to claim 1, wherein the molten, crude ε-caprolactam is obtained by gas phase Beckmann rearrangement of cyclohexanone oxime in the presence of a solid catalyst.

23. The process according to claim 1, further comprising the step of:
(xii) allowing the ε-caprolactam obtained in the solid-liquid separation step (ii) to contact with hydrogen in the presence of a hydrogenation catalyst.

24. The process according to claims 13, further comprising the step of:
(xi i)' allowing the ε-caprolactam obtained after the washing step (vi) to contact with hydrogen in the presence of a hydrogenation catalyst.

25. The process according to claim 1, wherein the molten, crude ε-caprolactam contains at least one impurity selected from the group consisting of 10 ppm or more of cyclohexanone oxime, 10 ppm or more of 1,2,3,4,6,7,8,9-octahydrophenazine and 25 ppm or more of 3-N-methyl-4,5,6,7-tetrahydrobenzimidazole and/or 25 ppm or more of caprenolactams, based on the ε-caprolactam.

26. The process according to claim 23, wherein the ε-caprolactam obtained after the hydrogenation step (xii) contains less than 10 ppm of cyclohexanone oxime, less than 10 ppm of 1,2,3,4,6,7,8,9-octahydrophenazine, less than 25 ppm of 3-N-methyl-4,5,6,7-tetrahydrobenzimidazole and/or less than 25 ppm of caprenolactams, based on the ε-caprolactam.

27. The process according to claim 24, wherein the ε-caprolactam obtained after the hydrogenation step (xii)' contains less than 10 ppm of cyclohexanone oxime, less than 10 ppm of 1,2,3,4,6,7,8,9-octahydrophenazine, less than 25 ppm of 3-N-methyl-4,5,6,7-tetrahydrobenzimidazole and/or less than 25 ppm of caprenolactams, based on the ε-caprolactam.

28. The process according to claim 1, wherein the molten, crude ε-caprolactam and the solvent are mixed with each other at a temperature of from 40° C. to about 60° C.

29. The process according to claim 1, wherein the molten, crude ε-caprolactam and the solvent are mixed with each other at a temperature of from 50° C. to about 60° C.

30. The process according to claim 1, wherein the solvent comprising an aliphatic hydrocarbon has a temperature of from about −30° C. to about 30° C, while being poured.

31. The process according to claim 1, wherein the solvent comprising an aliphatic hydrocarbon has a temperature of from about −30° C. to about 5.5° C., while being poured.

32. The process according to claim 1, wherein the molten, crude ε-caprolactam solvent has a temperature of from about 55° C. to about 80° C., while being poured.

* * * * *